(12) United States Patent
Satoh et al.

(10) Patent No.: US 11,111,213 B2
(45) Date of Patent: Sep. 7, 2021

(54) METHOD FOR PRODUCING METHIONINE

(71) Applicant: SUMITOMO CHEMICAL COMPANY, LIMITED, Tokyo (JP)

(72) Inventors: Yoshitaka Satoh, Niihama (JP);
Norihito Omoto, Niihama (JP);
Yoshiyuki Koizumi, Niihama (JP);
Naoya Yamashiro, Niihama (JP);
Ryousuke Katagami, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/608,002

(22) PCT Filed: Apr. 27, 2018

(86) PCT No.: PCT/JP2018/017212
§ 371 (c)(1),
(2) Date: Dec. 3, 2019

(87) PCT Pub. No.: WO2018/199295
PCT Pub. Date: Nov. 1, 2018

(65) Prior Publication Data
US 2021/0101865 A1    Apr. 8, 2021

(30) Foreign Application Priority Data

Apr. 27, 2017  (JP) .............................. JP2017-087752

(51) Int. Cl.
*C07C 319/28* (2006.01)
*C07C 319/20* (2006.01)
*C07C 323/58* (2006.01)

(52) U.S. Cl.
CPC .......... *C07C 319/28* (2013.01); *C07C 319/20* (2013.01); *C07C 323/58* (2013.01)

(58) Field of Classification Search
None
See application file for complete search history.

(56) References Cited

U.S. PATENT DOCUMENTS 8,101,797 B2 * 1/2012 Koizumi ............... C07C 319/28
562/559
8,217,197 B2 * 7/2012 Koizumi ............... C07C 319/20
562/559

(Continued)

FOREIGN PATENT DOCUMENTS

CN      101602700 A    12/2009
CN      101735125 A     6/2010

(Continued)

OTHER PUBLICATIONS

International Preliminary Report on Patentability and the Written Opinion of the International Searching Authority for International Application No. PCT/JP2018/017212, dated Oct. 29, 2019.

(Continued)

*Primary Examiner* — Amy C Bonaparte
(74) *Attorney, Agent, or Firm* — Birch, Stewart, Kolasch & Birch, LLP

(57) ABSTRACT

The present provides a method for producing methionine which is characterized by a crystallization step in which carbon dioxide is introduced into a reaction solution containing an alkali salt of methionine which is obtained by hydrolyzing 5-[2-(methylthio)ethyl] imidazoline-2,4-dione in the presence of an alkali compound, thereby precipitating the methionine, and further comprises a step of adding waste methionine to the reaction solution. The method of production of the present invention can improve a yield in the production of methionine.

4 Claims, 1 Drawing Sheet

(56) References Cited

U.S. PATENT DOCUMENTS

| | | | |
|---|---|---|---|
| 2003/0165611 A1* | 9/2003 | Chiavazza | A23K 20/142 |
| | | | 426/635 |
| 2010/0004486 A1 | 1/2010 | Koizumi et al. | |
| 2010/0121102 A1* | 5/2010 | Koizumi | C07C 319/28 |
| | | | 562/559 |
| 2010/0121103 A1 | 5/2010 | Koizumi et al. | |
| 2015/0038739 A1 | 2/2015 | Nishida et al. | |
| 2020/0140379 A1* | 5/2020 | Omoto | C07C 319/20 |

FOREIGN PATENT DOCUMENTS

| | | |
|---|---|---|
| CN | 104136418 A | 11/2014 |
| JP | 2001-340098 A | 12/2001 |
| JP | 2010-111641 A | 5/2010 |
| JP | 2013-173717 A | 9/2013 |

OTHER PUBLICATIONS

International Search Report for International Application No. PCT/JP2018/017212, dated Jul. 31, 2018.
Chinese First Office Action and Search Report (including an English translation thereof) issued in the corresponding Chinese Patent Application No. 201880027621.5 dated Nov. 19, 2020.
Singapore Office Action, dated Oct. 2, 2020, for Singapore Application No. 11201911236S.
Extended European Search Report for European Application No. 18790756.3, dated Jan. 12, 2021.
Chinese Second Office Action (including an English translation thereof) issued in the corresponding Chinese Patent Application No. 201880027621.5 dated Jun. 1, 2021.

* cited by examiner

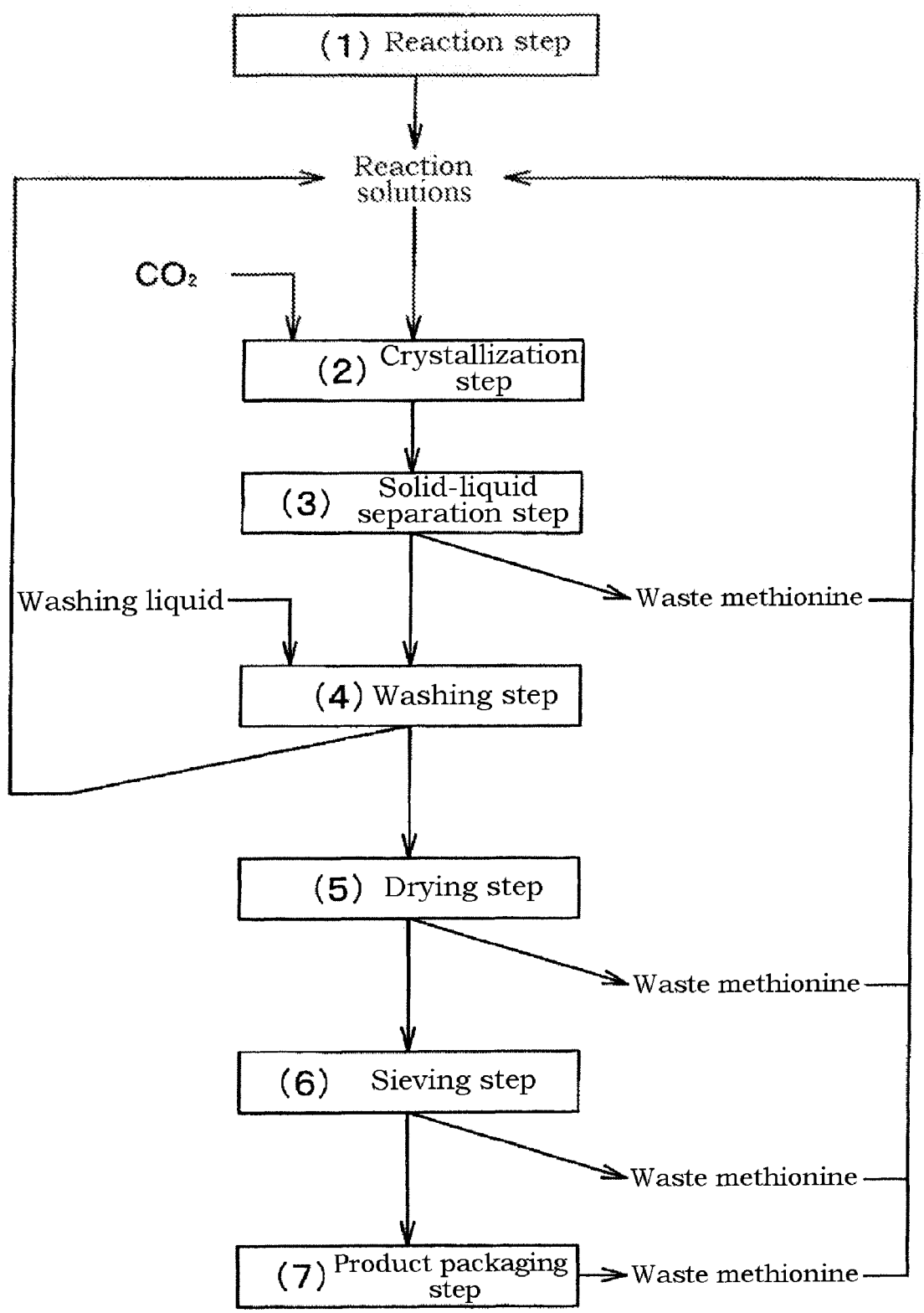

METHOD FOR PRODUCING METHIONINE

TECHNICAL FIELD

This application claims priority to and the benefit of Japanese Patent Application No. 2017-087752 filed Apr. 27, 2017, the entire contents of which are incorporated herein by reference.

The present invention relates to a method for producing methionine.

BACKGROUND ART

Methionine is an essential amino acid that cannot be synthesized in an animal body, and is widely used as a feed additive for animals, and also is industrially produced by a chemical plant.

There is disclosed a production method of methionine in which carbon dioxide gas is introduced into a reaction solution resulting from hydrolysis of 5-[2-(methylthio)ethyl] imidazoline-2,4-dione to precipitate out methionine, and it is separated by a solid-liquid separation (for example, see Patent document 1). Also, in order to reduce a loss in the production process, various studies have been done.

CITATION LIST

Patent Document

Patent Document 1: JP 2010-111641 A

SUMMARY OF THE INVENTION

Problems to be Solved by Invention

A study was made to reduce a methionine yield loss in its production step, focusing on the loss accompanying handling of methionine wet cake and powdered cake in a step or steps following a crystallization step to precipitate methionine by introducing carbon dioxide into a reaction solution containing an alkali salt of methionine resulting from hydrolysis of 5-[2-(methylthio)ethyl] imidazolidine-2, 4-dione in the presence of an alkali compound. The loss is caused, for example, by a fine powder of methionine generated in the drying step, and as the fine powder does not satisfy a predetermined size, it is not preferable to recover the fine powder and add it to the product as it is.

An object of the present invention is to provide a method for producing methionine that enables recovery of the loss (namely, waste methionine) as the product in the production method for preparing methionine.

Means to Solve Problems

The present inventors have intensively studied, and as a result, have found a method for recovering waste methionine, which is a fine powder methionine resulting in the step(s) following the crystallization step for precipitating methionine and had led to a loss of methionine by discharging as a waste methionine without being recovered from the production step, and found that methionine can be produced by adding the recovered methionine to the reaction solution (that is, reaction solution after hydrolysis), thereby enabling reduction of the loss.

The present invention includes the following embodiments.

The method for producing methionine as used herein (hereinafter, referred to as "Method for producing methionine of the present invention") is a method for producing methionine comprising a crystallization step in which carbon dioxide is introduced into a reaction solution containing an alkali salt of methionine which is obtained by hydrolyzing 5-[2-(methylthio)ethyl]imidazoline-2,4-dione in the presence of an alkali compound to precipitate methionine, wherein the method comprises a step of adding waste methionine to the reaction solution (the first aspect).

The second aspect of the present invention provides a method for producing methionine according to the first aspect wherein the waste methionine is methionine contained in mother liquor that is separated by a solid-liquid separation for separating the precipitated methionine in the crystallization step.

The third aspect of the present invention provides a method for producing methionine according to the first or the second aspect, wherein the step of adding the waste methionine to the reaction solution is a step of dissolving the waste methionine in the reaction solution.

The fourth aspect of the present invention provides a method for producing methionine according to the first aspect or the second aspect, wherein the step of adding the waste methionine to the reaction solution is a step of dissolving the waste methionine in water, and adding the resulting solution to the reaction solution.

The fifth aspect of the present invention provides a method for producing methionine according to any one of the first aspect to the fourth aspect, which comprises separating the precipitated methionine in the crystallization step by a solid-liquid separation, a washing step in which the methionine obtained by the solid-liquid separation is washed, and further comprises adding the washing liquid separated in the washing step to the reaction solution.

The six aspect of the present invention provides a method for producing methionine according to any one of the first aspect to the fifth aspect, which comprises, after a) the crystallization step, b) a step of subjecting the reaction solution containing precipitated methionine resulting in the crystallization step to a solid-liquid separation to obtain methionine and mother liquor, c) a step of recovering the methionine by filtration contained in mother liquor obtained by the solid-liquid separation step, d) a step of drying the methionine obtained by the solid-liquid separation to obtain the dried methionine, e) a step of sieving the dried methionine to obtain sieved methionine, f) a step of packaging the sieved methionine powders to obtain a packaged methionine product, and g) a step of transporting methionine between each of the steps c) to f), wherein the waste methionine supplied to the hydrolysis reaction step further includes at least one recovered methionine selected from the group consisting of methionine discharged out of the system due to exhaust in the drying process, the fine powdered methionine passed through a sieve mesh in a sieving step, methionine that is soared when filling containers with methionine in the product packaging step, and methionine discharged in each of the transporting steps.

According to the present invention, the methionine that was lost so far in the production process can be recovered as a methionine that can meet product standards, thereby improving a yield in the production of methionine.

BRIEF DESCRIPTION OF DRAWINGS

The FIGURE indicates an example of the flowchart of recovery of waste methionine in the production method according to one embodiment of the production method as used herein.

MODE FOR CARRYING OUT THE INVENTION

A production method of methionine as used herein is explained. The FIGURE illustrates the flowchart of recovery of waste methionine in the production method according to one embodiment as used herein. Here the embodiment described below exemplifies a method for producing methionine.

In the descriptions used herein, 5-[2-(methylthio)ethyl] imidazolidine-2,4-dione as a starting material is hydrolyzed in the presence of an alkali compound to obtain a reaction solution containing methionine as an alkali salt (hereinafter, referred to as "the present reaction solution") [(1) Reaction step (sometimes referred to as "hydrolysis reaction step")].

The 5-[2-(methylthio)ethyl]imidazolidine-2,4-dione as a starting material can be prepared by, for example, reacting 2-hydroxy-4-methylthiobutanenitrile with ammonia and carbon dioxide, or ammonia carbonate.

Examples of alkali compound include potassium hydroxide, sodium hydroxide, potassium carbonate, and potassium hydrogencarbonate, and as needed, two or more kinds thereof can be used. The amount of the alkali compound is usually 2 to 10 mols, preferably 3 to 6 mols as potassium or sodium per mole of 5-[2-(methylthio)ethyl]imidazolidine-2,4-dione. The amount of water is usually 2 to 20 parts by weight part by weight of 5-[2-(methylthio)ethyl]imidazolidine-2,4-dione.

The hydrolysis reaction in the reaction step is carried out in a continuous or batch reactor in a stirring style or a non-stirring style.

The hydrolysis reaction is preferably conducted by heating to about 150 to 200° C. under a pressurized pressure of about 0.5 to 1 MPa as a gauge pressure. The reaction time is usually 10 minutes to 24 hours.

In order to take out methionine from the reaction solution thus obtained, carbon dioxide is introduced into the present reaction solution to precipitate methionine [(2) crystallization step].

In the crystallization step, the procedure is performed, in which carbon dioxide is introduced into the present reaction solution to precipitate methionine. Carbon dioxide is absorbed into this reaction solution by introducing carbon dioxide, thereby alkali salt of methionine is precipitated as free methionine.

The introduction of carbon dioxide is preferably conducted under a gauge pressure of usually 0.1 to 1.0 MPa, preferably 0.2 to 0.5 MPa.

The crystallization temperature is usually 0 to 50° C., preferably 10 to 30° C. The crystallization time may be indicated by a time until the reaction solution is saturated with carbon dioxide and methionine is sufficiently precipitated, and is usually 10 minutes to 24 hours.

The embodiment of the present invention encompasses a step in which waste methionine is added to this reaction solution (hereinafter, referred to as "step 1"). In the present specification, "waste methionine" means a loss of methionine found in any steps after the crystallization step in which carbon dioxide is introduced into the reaction solution to precipitate methionine among various loss of methionine in the production steps. More specifically, such methionine includes a fine powder methionine, which has been discharged from the methionine production steps. Examples of the step performed after the crystallization step include a solid-liquid separation step, a drying step, a sieving step, a transporting step, and a product packaging step. Examples of the waste methionine include methionine discharged to the outside of the system along with exhaust or drainage. More specific examples of the methionine include methionine that is contained in the mother liquor which is separated in the solid-liquid separation step in which the methionine precipitated by introducing carbon dioxide into the reaction solution and the mother liquor are separated, methionine that is discharged out of the system with exhaust in the drying step, methionine that has passed through the mesh of the sieve in the sieving step, methionine that has been pulverized in the transporting step, and methionine that is soared when the methionine is charged into a container in the product packaging step. In the step 1, waste methionine recovered by the method described below is added to the present reaction solution.

In the step 1, waste methionine is dissolved in the present reaction solution, alternatively waste methionine is dissolved in separately prepared water, and then added to the present reaction solution. When the waste methionine is dissolved in the present reaction solution, the step 1 is conducted by carrying the present reaction solution to the vicinity where waste methionine is recovered and dissolving it in the present reaction solution which is carried, and returning it to the reaction process apparatus, alternatively the waste methionine is carried into a reaction step apparatus and is dissolved in the present reaction solution. When methionine is added to the present reaction solution, the temperature of the present reaction solution is usually 10 to 200° C., and pH is usually 9 to 12.

The methionine that is precipitated in the crystallization step is separated by a solid-liquid separation [(3) solid-liquid separation step].

In the solid-liquid separation step, methionine and mother liquor are obtained by performing filtration or decantation and the like. In the solid-liquid separation step, some fine powdered methionine that could not be separated may be remained in mother liquor. In this case, the mother liquor can be filtered with a filter to recover the methionine contained in mother liquor. In particular, when a solid-liquid separation step is conducted by a centrifugation, the amount of fine powdered methionine contained in mother liquor tends to increase, it is preferable to recover the methionine by filtering the mother liquor with a filter. As the filter, a filter having an air permeability of 0.1 to 1000 $cc/cm^2/s$ is usually used, preferably used is 0.5 to 500 $cc/cm^2/s$. The method for measuring the air permeability of the filter is conducted according to the method described in the air permeability section of JIS L 1096: 2010, 8.26. The amount of methionine contained in the mother liquor which is separated in the solid-liquid separation step is usually 0.1 to 15% (% by weight based on the methionine precipitated in the crystallization step). Since the recovered methionine thus obtained is wet, it is necessary to dry it to be added to the product, however, in order to save energy required for drying, in the present invention, the wet methionine may be added as it is to the present reaction solution.

The methionine obtained by solid-liquid separation is usually subjected to a washing step [(4) washing step].

Examples of the washing method include a method in which a washing liquid is sprayed on methionine with a nozzle, and a method in which the washing liquid is added to methionine and then the mixtures is stirred. As the washing liquid, a liquid which hardly dissolves methionine is used, and a saturated aqueous solution of methionine is preferably used. This saturated aqueous solution of methionine may be prepared by dissolving waste methionine in water. Further, the used washing liquid is separated and added to the present reaction solution, thereby methionine contained in the washing liquid can be precipitated and recovered in the crystallization step.

The methionine which is washed in the washing step is usually subjected to a drying step [(5) drying step]. The operation of drying methionine in the drying step is preferably conducted by heating to about 50 to 160° C. under slight reduced pressure, atmospheric pressure or under pressurized pressure, and preferably, the drying time is usually 10 minutes to 24 hours. In the drying step, the fine powdered methionine is discharged out of the system along with the exhaust, so that the methionine can be collected and recovered by a bag filter. The amount of methionine which is discharged out of the system in the drying step is usually 0.1 to 20% (% by weight based on methionine precipitated in the crystallization step). The recovered methionine is subjected to the step 1.

The methionine after drying is subjected to a sieving step for separating methionine that does not satisfy a predetermined size if necessary [(6) sieving step].

In the sieving step, methionine separated using a sieve can be recovered. The amount of methionine separated in the sieving step is usually from 0.1 to 25% (% by weight based on methionine precipitated in the crystallization step). The recovered methionine is subjected to the step 1.

When methionine is transported as a product, methionine is filled in containers such as plastic bags and flexible containers [(7) product packaging step].

In this embodiment, the fine powdered methionine which has soared at this filling time can be sucked and collected by a bag filter. The amount of fine powdered methionine recovered in the product packaging step is usually 0.1 to 30% (% by weight based on methionine precipitated in the crystallization process). The recovered methionine is subjected to the step 1.

Although not shown in the FIGURE, methionine which is pulverized in the transporting step can also be collected and subjected to the step 1.

Examples of the transport path include a transport path for transporting methionine obtained in the solid-liquid separation step to the washing step, a transport path for transporting methionine washed in the washing step to the drying step, a transport path for transporting methionine dried in the drying step to the sieving step, and a transport path for transporting methionine separated in the sieving step to the product packaging process. The transporting method in these transporting steps is not particularly limited, and includes transportation such as a belt conveyor, a screw conveyor, pneumatic transportation, or transportation by bucket. The refined methionine in the transporting step includes finely divided methionine caused by a contact with the bucket in the case of transportation using a bucket and a collision with a pipe wall in the case of pneumatic transportation. The methionine pulverized in these transportation steps can be collected by a bag filter after being classified with a cyclone as necessary. The amount of methionine to be pulverized in the transport process is usually 0.1 to 5% (% by weight based on methionine precipitated in the crystallization process). The recovered methionine is subjected to the step 1.

EXAMPLES

Next, examples of the present invention are shown below, however, the present invention is not limited thereto. Unless otherwise specified, parts indicated in the examples represent parts by weight, and parts/hr represents a flow rate per hour unless otherwise specified.

Example 1

A 120.7 part by weight/hr of aqueous solution containing 6.5% by weight of 5-[2-(methylthio)ethyl] imidazolidine-2,4-dione, 2.1% by weight of methionine, and 5.0% by weight of potassium was charged into a reaction vessel, and reacted at a gauge pressure of 0.88 MPa at 173 to 178° C. for a residence time of 1 hour to obtain a reaction solution. One hundred (100) parts by weight of the reaction solution was transported to a crystallization tank, and carbon dioxide was introduced into the reaction solution at 20° C. under a gauge pressure of 0.35 MPa, and methionine was precipitated to obtain a slurry containing 9.7 parts by weight/hr of the precipitated methionine. The slurry was centrifuged with a centrifugal effect of 1000 G to obtain a methionine wet cake and a mother liquor. The obtained mother liquor was filtered with a polypropylene filter (air permeability 36 $cc/cm^2/s$, average pore size 15 μm, twilled weave) to recover methionine contained in the mother liquor. The recovered amount of methionine contained in the mother liquor was 1.2 parts by weight/hr as a dry weight. The methionine discharged out of the system in the drying step and the methionine pulverized in the transport step respectively were classified by a cyclone, and then were collected by a polypropylene filter. The recovered amount of methionine discharged out of the system in the drying step was 0.5 parts by weight/hr, and the recovered amount of methionine finely powdered in the transportation step was 1.1 parts by weight/hr.

Example 2

Two point eight (2.8) parts by weight/hr of these recovered methionine are put into a stirring tank in a powder state, and are dissolved in 100 parts by weight/hr of the reaction solution at a liquid temperature of 25° C., and are then transported to the crystallization tank. To the resulting solution which is obtained by dissolving 2.8 parts by weight/hr of methionine into 100 parts by weight/hr of the reaction solution, carbon dioxide is introduced in a similar manner to the example 1 to precipitate methionine.

The recovered methionine 2.8 parts by weight/hr corresponds to 29% by weight of 9.7 parts by weight/hr of methionine precipitated in the crystallization step, which means that if a waste methionine is not recovered, 29% by weight is lost.

The invention claimed is:
1. A method for producing methionine comprising
a) a crystallization step in which carbon dioxide is introduced into a reaction solution containing an alkali metal salt of methionine, which is obtained by hydrolyzing 5-[2-(methylthio)ethyl] imidazolidine-2,4-dione in the presence of an alkali compound selected from the group consisting of potassium hydroxide, sodium hydroxide, potassium carbonate, and potassium hydrogencarbonate, to precipitate methionine,
b) a step of subjecting the reaction solution containing precipitated methionine resulting in the crystallization step to a solid-liquid separation to obtain methionine and mother liquor,
c) a step of recovering methionine from the mother liquor by filtration, d) a step of drying the methionine obtained by step c) to obtain dried methionine, wherein the drying step also produces an exhaust, e) a step of sieving the dried methionine to obtain sieved methionine, f) a step of packaging the sieved methionine powders to obtain a packaged methionine product, and g) a step of transporting methionine between each of the steps c) to f), wherein the method comprises a step of adding waste methionine to the reaction solution, wherein the waste methionine supplied to the hydrolysis reaction solution includes recovered methionine in step c), and at least one recovered methionine selected from the group consisting of methionine discharged out of the system due to exhaust in the drying step, fine powdered methionine passed through a sieve mesh in the sieving step, methionine that is soared when filling a container with methionine in the product packaging step, and methionine lost during any of the transporting steps.

2. The method for producing methionine according to claim 1, wherein the step of adding the waste methionine to the reaction solution is conducted by dissolving the waste methionine in the reaction solution.

3. The method for producing methionine according to claim 1, wherein the step of adding the waste methionine to the reaction solution is conducted by dissolving the waste methionine in water, and then adding the dissolved methionine to the reaction solution.

4. The method for producing methionine according to claim 1, wherein step c) further comprises a washing step in which the methionine obtained by the solid-liquid separation is washed, and further comprises adding the washing liquid separated in the washing step to the reaction solution.

* * * * *